(12) United States Patent
Taylor (10) Patent No.: US 8,323,282 B2
(45) Date of Patent: Dec. 4, 2012

(54) ACCESSORY DEVICE FOR AN ORTHOPEDIC FIXATOR

(76) Inventor: Jeffrey Taylor, Roanoke, TX (US)

( * ) Notice: Subject to any disclaimer, the term of this patent is extended or adjusted under 35 U.S.C. 154(b) by 0 days.

(21) Appl. No.: 13/269,879

(22) Filed: Oct. 10, 2011

(65) Prior Publication Data

US 2012/0029516 A1 Feb. 2, 2012

Related U.S. Application Data

(63) Continuation-in-part of application No. 12/433,360, filed on Apr. 30, 2009, now abandoned.

(51) Int. Cl.
*A61B 17/00* (2006.01)
*A61F 5/00* (2006.01)
*A61F 5/01* (2006.01)

(52) U.S. Cl. .................. 606/59; 602/23; 602/27; 36/110

(58) Field of Classification Search ............. 606/53–59; 602/23, 27; 128/882; 2/16, 20, 22, 59; 36/101, 36/1, 89, 110, 109
See application file for complete search history.

(56) References Cited

U.S. PATENT DOCUMENTS

| | | | | |
|---|---|---|---|---|
| 4,351,324 A | * | 9/1982 | Bronkhorst | 602/27 |
| 5,507,106 A | * | 4/1996 | Fox | 36/103 |
| 5,961,477 A | * | 10/1999 | Turtzo | 602/27 |
| 6,158,150 A | * | 12/2000 | Morris et al. | 36/115 |
| 6,277,087 B1 | * | 8/2001 | Hess et al. | 602/27 |
| D540,516 S | * | 4/2007 | Weitzman | D2/953 |
| 7,887,495 B2 | * | 2/2011 | Boyd et al. | 602/3 |
| 2002/0188239 A1 | * | 12/2002 | Turtzo | 602/27 |
| 2005/0059968 A1 | * | 3/2005 | Grant et al. | 606/54 |
| 2005/0131324 A1 | * | 6/2005 | Bledsoe | 602/23 |
| 2005/0172517 A1 | * | 8/2005 | Bledsoe et al. | 36/110 |
| 2008/0132817 A1 | * | 6/2008 | Vito | 602/23 |
| 2009/0043234 A1 | * | 2/2009 | Bledsoe et al. | 602/23 |
| 2009/0105621 A1 | * | 4/2009 | Boyd et al. | 602/3 |
| 2009/0124947 A1 | * | 5/2009 | Grant | 602/23 |
| 2009/0275944 A1 | * | 11/2009 | Huebner et al. | 606/54 |

* cited by examiner

*Primary Examiner* — Alvin Stewart
*Assistant Examiner* — Jacqueline Johanas
(74) *Attorney, Agent, or Firm* — Charles D. Gunter, Jr.

(57) ABSTRACT

An accessory device for an external orthopedic fixator where the fixator has an external frame made up of frame components which surround the lower leg and ankle of a patient with one or more transfixation wires fixed thereto. The accessory device includes a walking plate which connects to one of the fixator frame components for supporting the sole of a patient's foot. The accessory device also includes a companion shroud which is wrapped about the fixator with the fixator being received within the interior of the shroud. The shroud has a width and height which are sufficient to conceal the fixator within the shroud interior. The shroud has fasteners which allow it to be easily installed and removed from about the fixator.

6 Claims, 8 Drawing Sheets

ACCESSORY DEVICE FOR AN ORTHOPEDIC FIXATOR

CROSS-REFERENCE TO RELATED APPLICATION

The present application is a continuation-in-part of earlier filed application Ser. No. 12/433,360, filed Apr. 30, 2009.

BACKGROUND OF THE INVENTION

1. Field of the Invention

This invention relates generally to therapeutic devices used for fixating and immobilizing limbs, particularly a patient's foot and ankle and, more specifically, to a novel walking plate for an Ilizarov-type external fixator and to an accessory cover or shroud for a fixator of this general type.

2. Description of the Prior Art

There are many types and classes of braces and other orthopedic devices for fixating and immobilizing a patient's limbs due to various medical conditions. For example, when a bone is fractured, it is often necessary to hold the fragments of the bone together to allow for correct healing. If this is not done, problems such as misalignment or poor healing can occur.

In the field of foot and ankle surgery and recovery, multiple options exist for stabilizing a patient's foot after surgery. One option, referred to in the field as a "fixator," has transfixation wires, pins or screws that extend into and through bone segments in order to stabilize the bones. The external fixator typically takes the form of a steel rod, collar, or other external frame element spanning across the fracture which is fixed to the bone fragments using the wires, pins or screws. The frame elements are located outside the body, while the pins or similar elements penetrate the skin and are fixed in the bone. Other external braces including a wide range of removable casts and ankle braces are also known.

One preferred class of external fixators is referred to in the field of orthopedics as the "Ilizarov" device, named for the inventor of the device. This device uses thin wires and external fixator frame components to properly place segments of bone for purposes of reconstruction of fractured or deformed extremities following orthopedic surgery. Frames used in these types of procedures are arranged crosswise in pairs or individually in each ring or ring-section level, whereby the various rings are connected to each other by means of rods and bolts. The intervals of the ring levels can be adjusted by rods whose lengths can be varied telescopically, or by bolts that can be adjusted. Frames of this type are now commonly in use for a variety of orthopedic applications including limb lengthening, stabilization and positioning of open fractures, and in the structural correction of a multitude of lower extremity deformities such as the correction of angulation, rotation and translation.

Another general type of orthopedic device that may be used as a therapeutic or surgical recovery brace is sometimes referred to informally as the "cam boot" and may resemble a ski boot in outward appearance. However, the cam boot functions as a type of functional splint or cast which holds the foot in a neutral position while healing takes place after a surgery. A cam boot is noninvasive and can, in some instances, successfully immobilize the extremity during the healing process. Also, cam boots are removable. While appropriate in many situations and for multiple types of surgeries, a cam boot is not an option when performing surgeries to correct many foot injuries or deformities.

While the Ilizarov-type device provides a much more stable platform for recovery in many surgical situations than the cam boot, the appearance of the external fixator with its cross wires, pins and ring elements can be embarrassing or unsightly to some wearers or observers. Additionally, the exposed nature of the embedded pins and the rings and other external fixator elements presents the added danger of accidentally bumping these components, causing pain and discomfort, or even additional injury to the patient.

A need exists for a walking plate of improved design which would be fastened directly to the fixator frame and which would support the patient's foot while walking and provide added stability for the entire assembly.

A need exists for such a walking plate which could easily be adapted to fit all of the commonly used fixators on the market today and which would be applicable to a variety of patient's and surgeon's preferences and utilization patterns.

A further need exists for such a walking plate having a specific angulation of cut of the walking platform for the most successful ambulation of the patient.

A need also exists for an effective cover or shroud for the Ilizarov fixator which would cooperate with the improved walking plate and essentially conceal the fixator while the fixator is in place on a patient, especially in public situations. The cover or shroud should be easily removable, as at night, and should be made of materials which provide adequate concealment, while also being durable and long lasting and which also add an element of additional protection to the wearer from accidental bumps or jolts.

SUMMARY OF THE INVENTION

It is therefore an object of the present invention to provide a cover or shroud and companion foot or walking plate for an Ilizarov type fixator which meets the aforementioned needs. More specifically, the accessory device of the invention is designed for use with an external orthopedic fixator used to stabilize a patient's foot and ankle, where the fixator has an external frame made up of a plurality of frame components which surround the lower leg and ankle of a patient with one or more transfixation wires fixed thereto.

The walking plate, which forms one element of the combination accessory device of the invention has an upper surface used for supporting the sole of a patient's foot and has an oppositely arranged lower surface and an intermediate thickness. The walking plate has a plurality of connector elements mounted thereon. The connector elements have exposed upper extents extending upwardly from the upper surface of the walking plate, the upper extents being matingly engageable with at least one of the frame components of the fixator for securing the walking plate to the fixator and for supporting the patient's foot. The walking plate also has a peripheral outer edge which includes a connector region.

In one form of the invention, the walking plate has a plurality of precisely located holes communicating the upper and lower surfaces thereof for receiving the connector elements. The location of the holes is predetermined to accept a variety of different manufacturer's fixator components of various sizes and spacings without further drilling or alteration of the foot plate. Preferably, the holes which communicate the upper and lower surfaces of the walking plate terminate in counterbores on the plate lower surface, the counterbores being sized to receive the heads of connecting bolts in recessed fashion. The bottom surface of the walking plate is also preferably provided with a rubber layer which forms a tread pattern for improved traction. In one form, the tread pattern comprises a series of undulating rows running longitudinally between opposing sides of the walking plate.

In one preferred form of the invention, the walking plate has a front and rear ambulation cut of specific angles designed to improve the ambulation of a patient during walking. Preferably, the walking plate is designed to have an approximate 30 degree angle extending proximally for approximately 2 centimeters back from a toe region of the walking plate and an approximate 15 degree angle extending distally back for approximately 4 centimeters from a heel region of the walking plate. These dimensions have been chosen to provide the most natural shape and configuration for ambulation with a foot and ankle locked into a 90 degree position by the associated fixator.

The other component of the accessory device of the invention comprises a flexible shroud having an overall width and height, an exterior and an interior. A longitudinal seam, running vertically from the top to the bottom of the shroud, allows the shroud to be wrapped about the fixator with the fixator being received within the interior of the shroud and then secured in place. The shroud width and height are sufficient to conceal the fixator when the fixator is so received. In one preferred form, the longitudinal seam of the shroud also includes a connector region for securing the shroud about the fixator.

In one form, the shroud has a lower peripheral edge which is provided with a connector region for matingly engaging the connector region of the walking plate. The longitudinal seam of the shroud can also be provided with a connector region for securing the shroud about the fixator. In one preferred form of the device, the connector regions on the lower peripheral edge of the shroud are snaps for engaging mating buttons on opposing sides of the walking plate. The connector region provided along the longitudinal seam of the shroud can conveniently comprise a mating region of hook and loop type fabric connector fabric. The assembled walking plate and shroud completely enclose the fixator from beneath and on all sides.

Additional objects, features and advantages will be apparent in the written description which follows.

DETAILED DESCRIPTION OF THE INVENTION

The preferred version of the invention presented in the following written description and the various features and advantageous details thereof are explained more fully with reference to the non-limiting examples included in the accompanying drawings and as detailed in the description which follows. Descriptions of well-known components and processes and manufacturing techniques are omitted so as to not unnecessarily obscure the principle features of the invention as described herein. The examples used in the description which follows are intended merely to facilitate an understanding of ways in which the invention may be practiced and to further enable those skilled in the art to practice the invention. Accordingly, the examples should not be construed as limiting the scope of the claimed invention.

Figure 1:
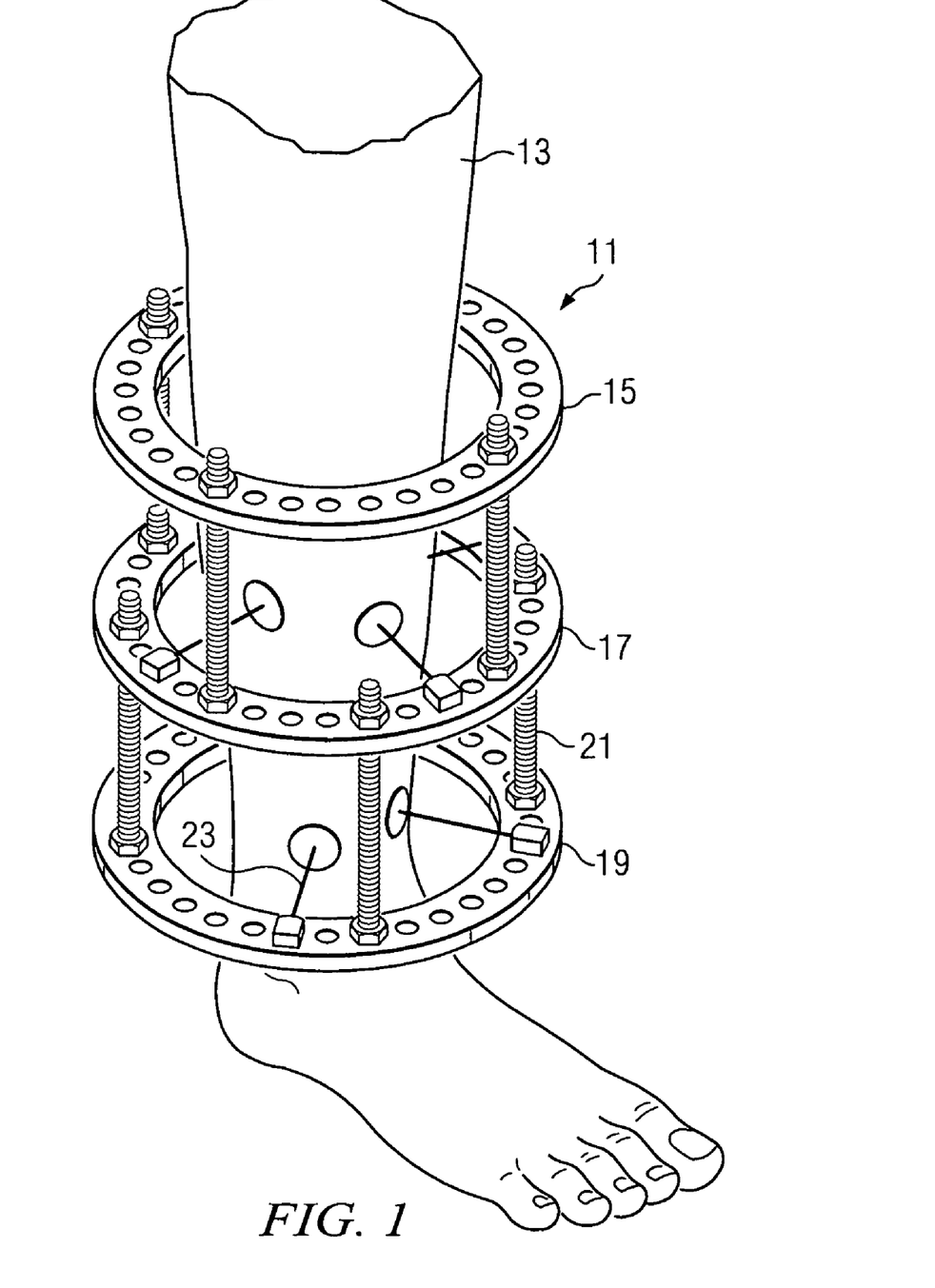
FIG. 1 is a perspective view of a portion of a human leg showing an Ilizarov-type orthopedic fixator in place on the ankle and lower leg of the patient.

Turning to FIG. 1, there is shown one form of an external fixator of the type under consideration, designated generally as 11, the fixator being received about the lower leg 13 of a patient. As will be evident from FIG. 1, the fixator 11 includes a plurality of frame components which take the form of stacked rings or collar elements 15, 17, 19, which, in this case, are held together by means of a series of threaded bolts 21. The collar elements 15, 17, 19, span across a fracture of the lower leg and are fixed to the bone fragments using wires, pins or screws, in this case wires 23. While different fixators may use, for example, various wires, pins, screws or like transfixation or cross-elements, in this discussion the term "wires" will be understood to mean any of these commonly used transfixation cross-elements. As shown in FIG. 1, the frame elements are located outside the body, while the wires or similar elements penetrate the skin and are fixed in the bone.

Figure 2:
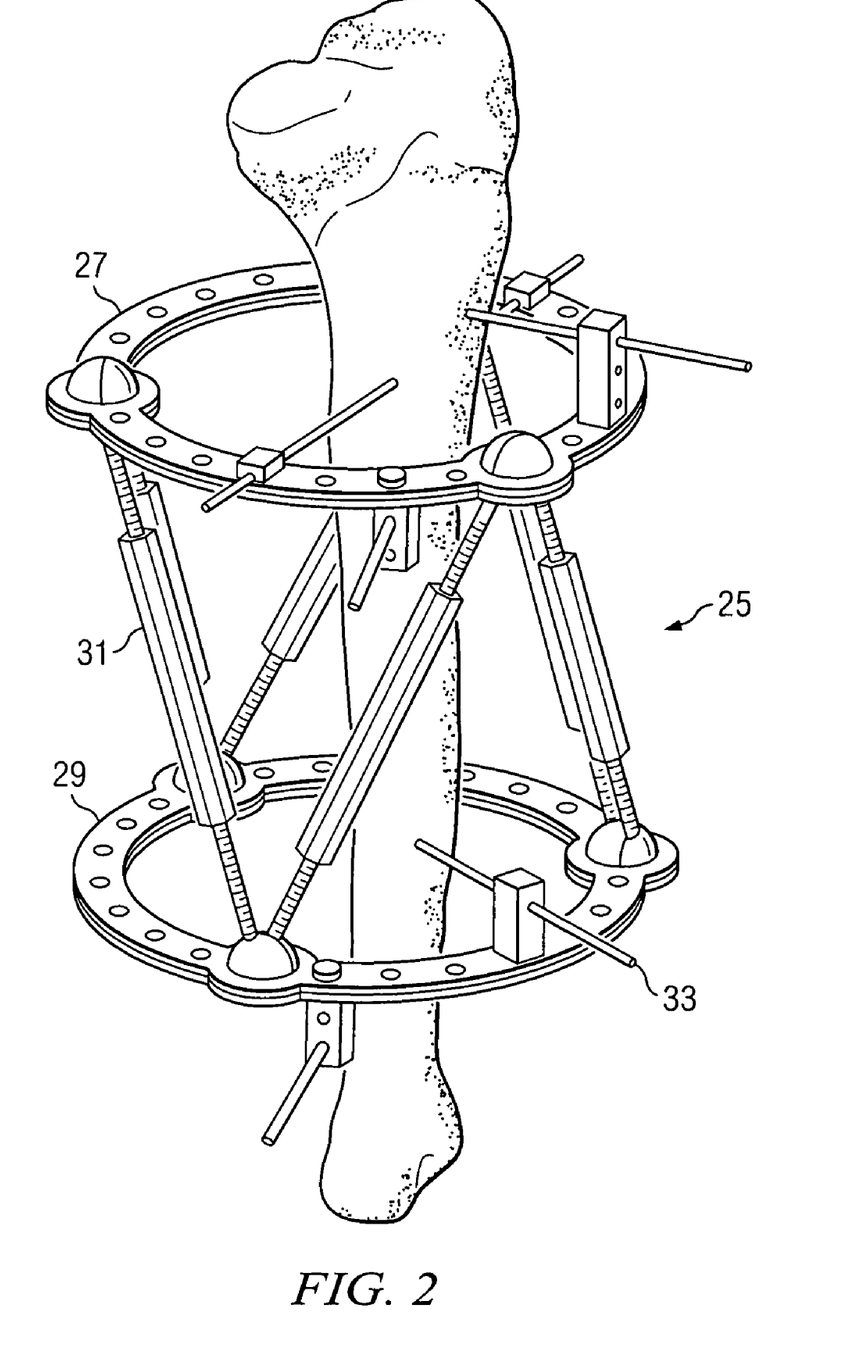
FIG. 2 is another view of an Ilizarov-type fixator showing the cross pins which penetrate the bone of the patient, with the bone being exposed for ease of illustration.

FIG. 2 is a simplified view of another Ilizarov-type fixator 25 which has upper and lower collar elements 27, 29, the collars being connected and supported by means of connecting bolt assemblies (e.g., assembly 31). The bone is shown exposed to illustrate the fact that the cross pins 33 actually penetrate the bone itself. It will be appreciated that there are a variety of Ilizarov-type devices that are arranged somewhat differently from those illustrated in FIGS. 2 and 3, but which all operate in a generally similar fashion.

Thus, with reference to FIG. 2, the intervals or spacing of the collar elements 27, 29 can be adjusted by movement of the adjusting bolt assemblies 31. As mentioned in the Background Discussion, frames of this type are now commonly in use for a variety of orthopedic applications including limb lengthening, stabilization and positioning of open fractures, and in the structural correction of a multitude of lower extremity deformities such as the correction of angulation, rotation and translation, and these general types of devices will be well known to those involved in the field of orthopedic surgery, as well as being described in a number of different medical texts and journal articles.

Figure 3:
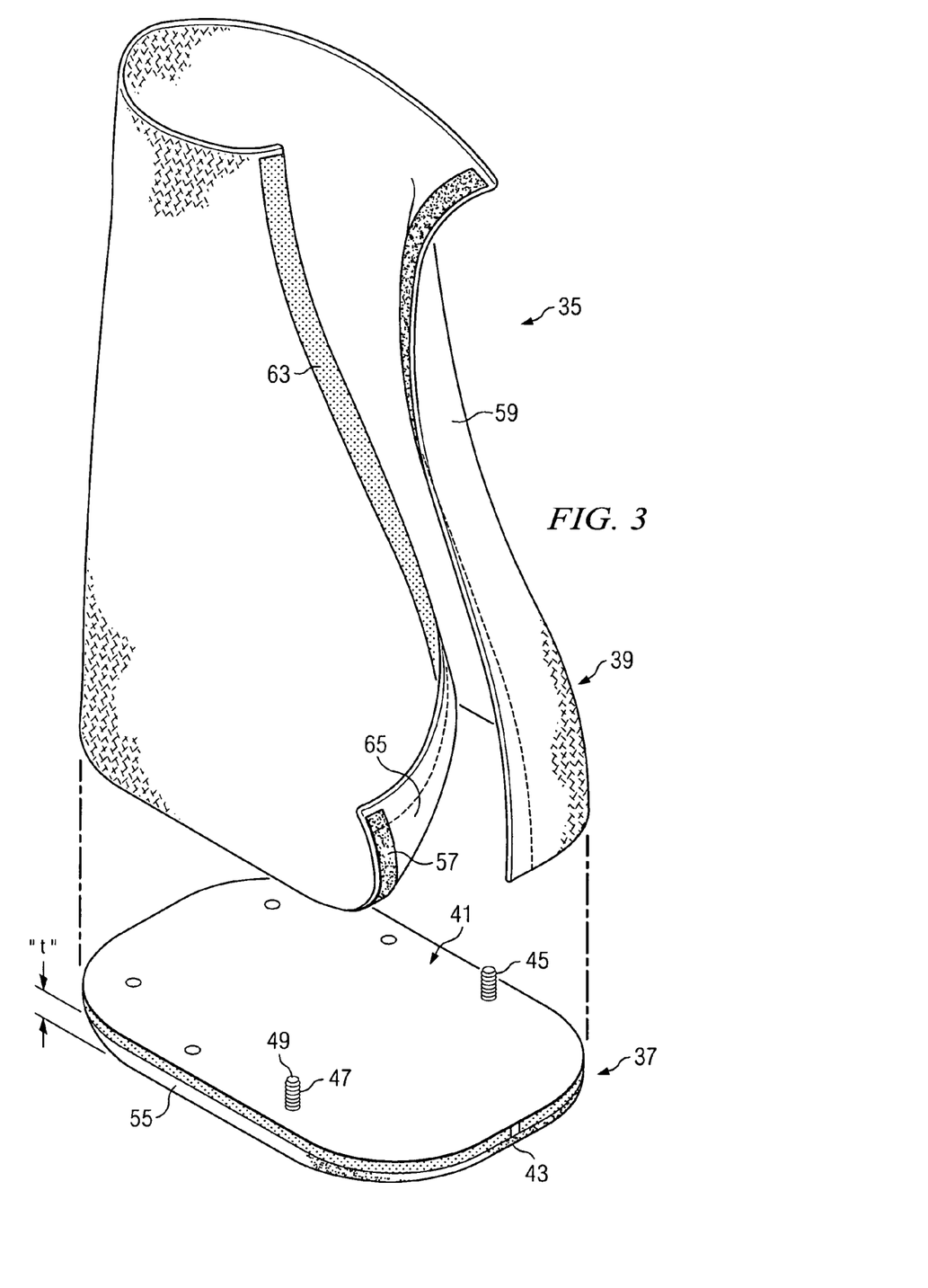
FIG. 3 is a perspective view of one version of the accessory device of the invention with the shroud portion thereof shown exploded from the base portion thereof.

Turning now to FIG. 3, there is shown one version of an orthopedic fixator accessory device of the invention, designated generally as 35. The accessory device 35 is intended to be used with an external orthopedic fixator of the type previously described which is used to stabilize a patient's foot and ankle, the fixator having an external frame made up of a plurality of frame components which surround the lower leg and ankle of a patient with one or more transfixation wires fixed thereto.

As shown in FIG. 3, the accessory device 35 of the invention is comprised of two cooperating components, a foot or walking plate 37 and a shroud 39. Turning first to the foot plate 37, it will be seen to be a generally planar member having an upper surface 41 used for supporting the sole of a patient's foot and having an oppositely arranged lower surface 43 and an intermediate thickness (shown as "t" in FIG. 3). In one preferred form, the foot plate 37 is constructed with a 4-ply configuration with ⅛ inch high grade rubber with grooves for the lower surface 43, then a ¼ inch layer of semi-rigid polypropylene, then a ⅛ inch flat layer of rubber, and finally a ⅛ inch layer of Plastozote™ as the top layer 41. Plastozote™ is a high quality, lightweight closed-cell crosslinked polyethylene "memory foam", manufactured by Zotefoams, PLC and is available commercially from a number of sources.

As can be seen in FIG. 3, the foot plate 37 has a plurality of connector elements, e.g., elements 45, 47, mounted thereon. The connector elements 45, 47 have exposed upper extents 49 extending upwardly from the upper surface 41 of the foot plate. The upper extents 49 are matingly engageable with at least one of the frame components of the fixator for securing the foot plate 37 to the fixator and for supporting the patient's foot. This is best illustrated in FIG. 4 of the drawings which shows a connector element upper extent 49 which is received within an opening in the frame collar element 51 and retained in position by the nut 53.

Returning briefly to FIG. 3, the foot plate 37 also has a peripheral outer edge which includes a connector region, illustrated in exaggerated fashion as the region 55 in FIG. 3. As will be explained in greater detail below, the connector region is used to temporarily affix the companion shroud 35 to the foot plate 37. The connector region can be, for example, covered with a hook and loop "Velcro™" type connector material which connects to a mating lower peripheral region (57 in FIG. 3) on the shroud.

Figure 4:
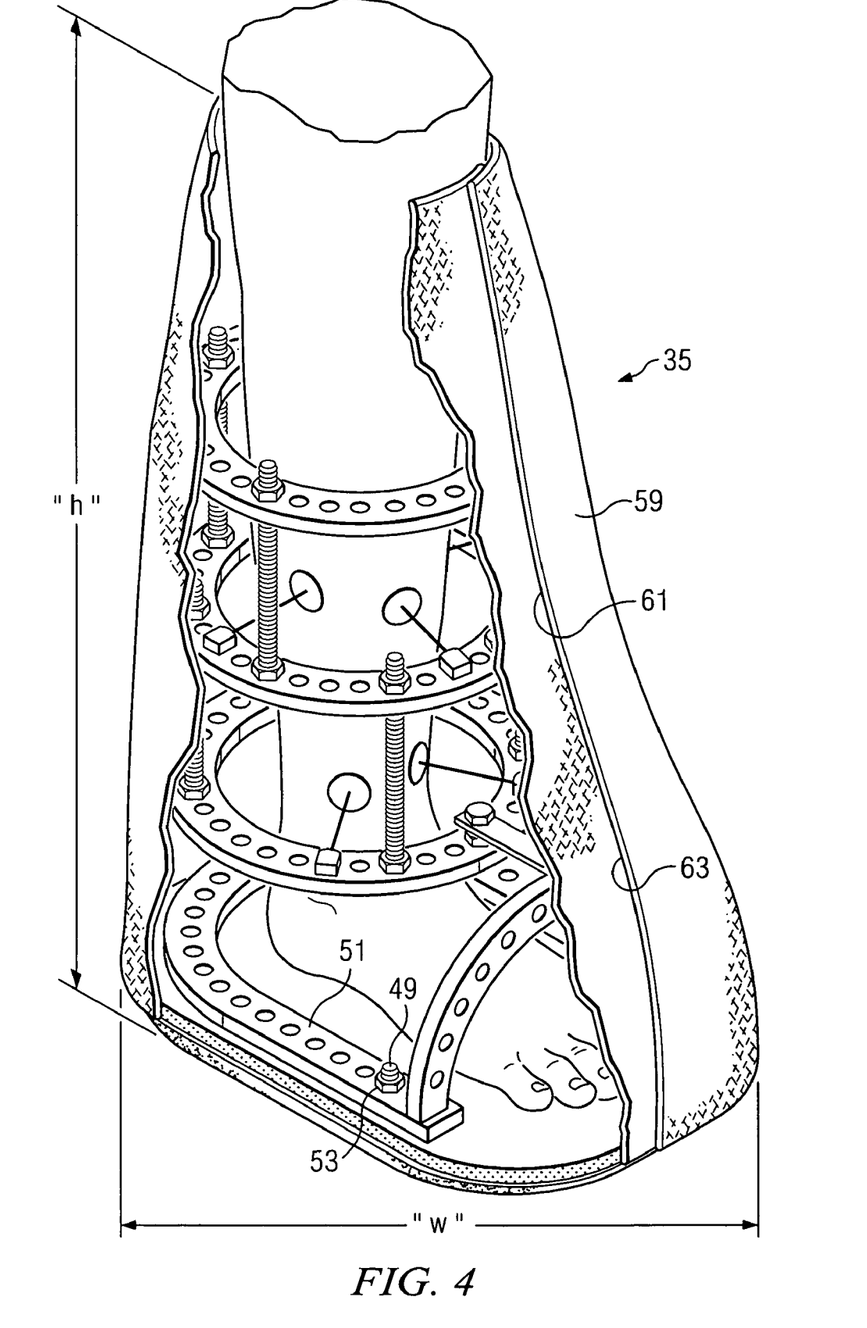
FIG. 4 is another perspective view of an accessory device of the invention in place on the lower leg of a patient, a portion of the shroud thereof being shown broken away for ease of illustration.

With reference to FIGS. 3 and 4, it can be seen that the flexible shroud 35 has an overall width ("w" in FIG. 4) and height ("h" in FIG. 4). The shroud also has an exterior 59, an interior 61, and a longitudinal seam 63 which allow the shroud to be wrapped about the fixator with the fixator being received within the interior 61 of the shroud. The shroud width and height are sufficient to conceal the fixator when the fixator is so received with the fixator being completely enclosed on all sides and from the bottom, by virtue of the foot plate 37. As has been mentioned, the shroud has a lower peripheral edge 57 which is provided with a connector region for matingly engaging the connector region of the foot plate 37. The longitudinal seam 63 of the shroud also includes a Velcro™ connector region for securing the shroud about the fixator. If desired, the longitudinal seam 63 and the peripheral edge 57 can be provided with additional connector elements, such as snap fastener type connector elements to further reinforce the positioning of the shroud about the fixator.

The shroud body can itself be formed of a variety of convenient materials. In one preformed form, the shroud body is formed of a synthetic fabric material, the interior of the shroud being provided with a layer of protective plastic (65 in FIG. 3) which reinforces and protects at least a portion of the interior surface thereof. Most preferably, the exterior of the shroud is a light weight, but tear resistant synthetic fabric with a thin sheet of flexible polypropylene on the interior side facing the fixator.

In use, the combination foot plate and shroud of the invention are used to temporarily conceal an external fixator of the type previously described. The foot plate is attached to at least a selected one of the fixator frame components so that the foot plate supports the patient's foot, as by passing the threaded bolts 45, 47 through the mating openings in the lower collar of the fixator and securing the bolts with nuts. The shroud 35 is then wrapped about the fixator and the patient's lower leg, whereby the fixator is concealed within the interior of the shroud. The shroud 35 is affixed to the foot plate by matingly engaging the connector region 57 on the lower peripheral edge of the shroud with the connector region 55 of the footplate 37. The shroud 35 is then further secured about the fixator by matingly engaging the connector regions 63 running along the longitudinal edges of the shroud seam.

With reference now to FIGS. 7-10 of the drawings, there is shown a further version of the accessory device of the invention which offers further improvements over the basic design shown in FIGS. 1-6. With reference first to the walking plate component (65 in FIGS. 7 and 8), it can be seen that the walking plate has a top surface 67, a bottom surface 69 and an intermediate thickness. The top surface 67 has a series of pre-drilled holes (such as hole 71 in FIG. 7) which are precisely drilled at dimensions measured from four or more different ring manufacturers to fit at least three different size foot plates. The hole spacing is also designed to fit circular rings, as well. In this way, a single foot plate can be used with any number of different manufacturer's fixator components, without having to inventory a number of different plates, or drill additional holes or make other on-site modifications to the foot plate.

Figure 9:
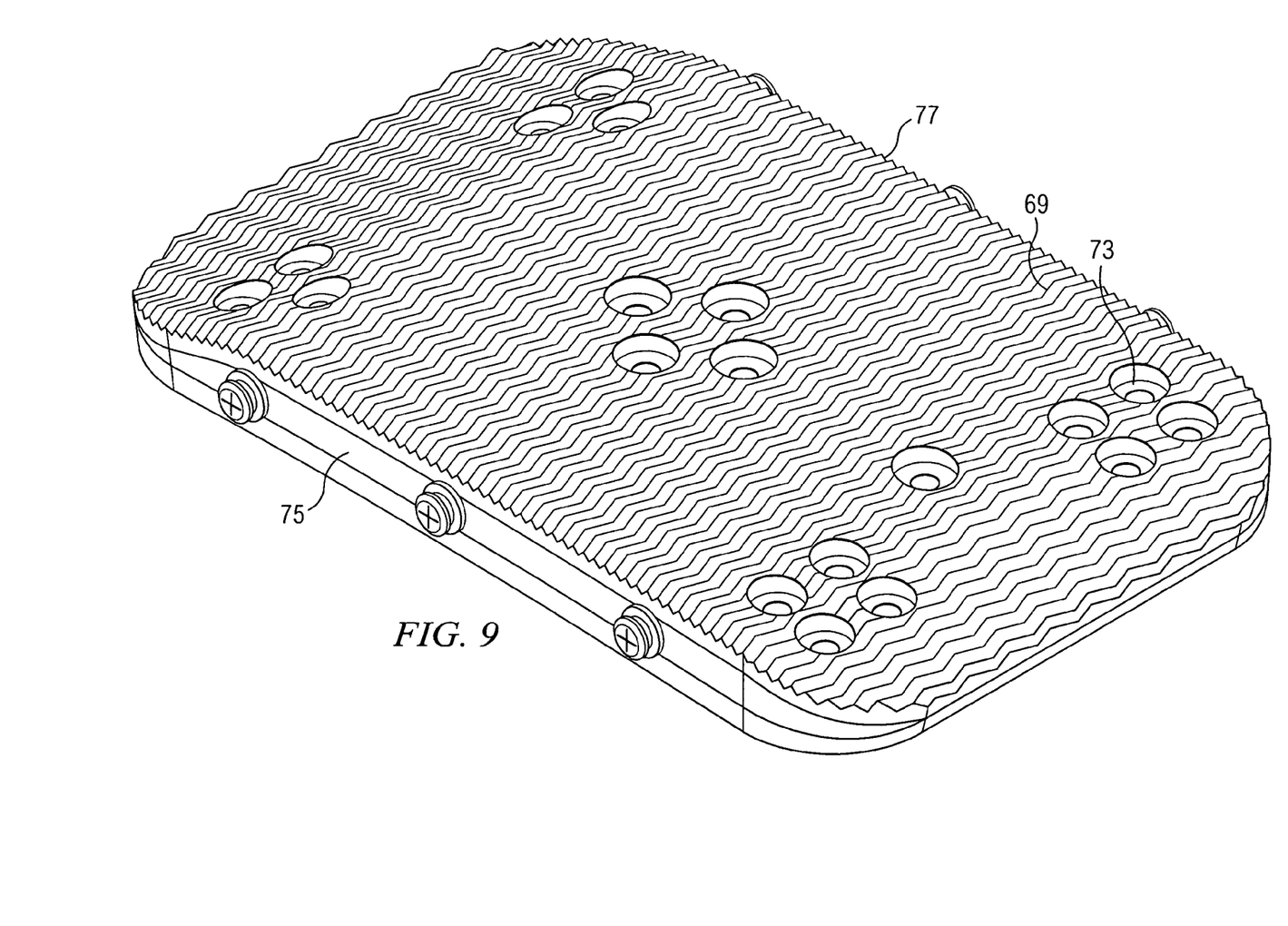
FIG. 9 is a bottom view of the walking plate of FIG. 7, showing the location of the holes which are pre-drilled to receive the bolts and nuts which are used to attach the walking plate to the fixator frame.

As can be seen in FIG. 9, the bottom surface 69 of the foot plate actually has counterbores 73 for receiving the attaching bolt heads. This depressed pattern on the bottom of the plate allows for added stability while walking and also avoids the necessity of walking directly on the hardware. The bottom surface 69, as shown in FIG. 9, has a rubber tread surface for added traction on a variety of walking surfaces. The preferred tread pattern is a series of undulating rows running longitudinally between the opposing sides 75, 77 of the walking plate.

Figure 8:
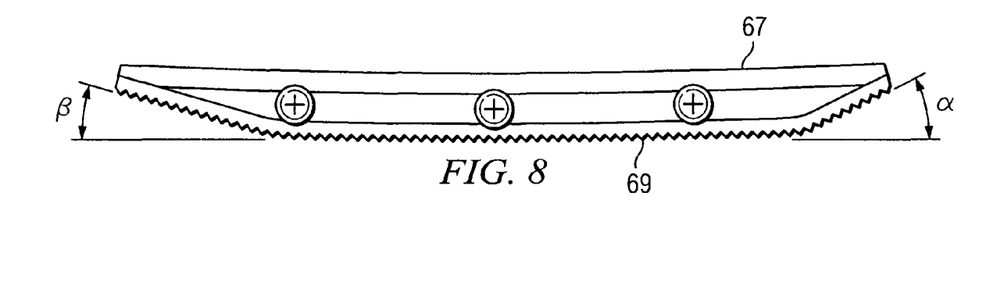
FIG. 8 is a side view of the walking plate of FIG. 7, showing the angulation of cut of the walking plate.

With reference to FIG. 8, the angulation of cut of the walking plate is unique and designed for the most successful ambulation for the patient. These dimensions have been determined to be approximately a 30 degree angle $\alpha$ extending proximally (back to the left as viewed in FIG. 8) for approximately 2 centimeters and an approximate 15 degree angle $\beta$ extending distally (back from the right as viewed in FIG. 8) for approximately 4 centimeters. As viewed in FIG. 8, the angle $\alpha$ is at the rear of the patient's foot when the plate is in place, while the angle $\beta$ is in the vicinity of the patient's toe. These dimensions have been found to be the most natural shape and configuration for ambulation with a foot and ankle locked into a 90 degree position as is the case with most fixator positions.

Figure 10:
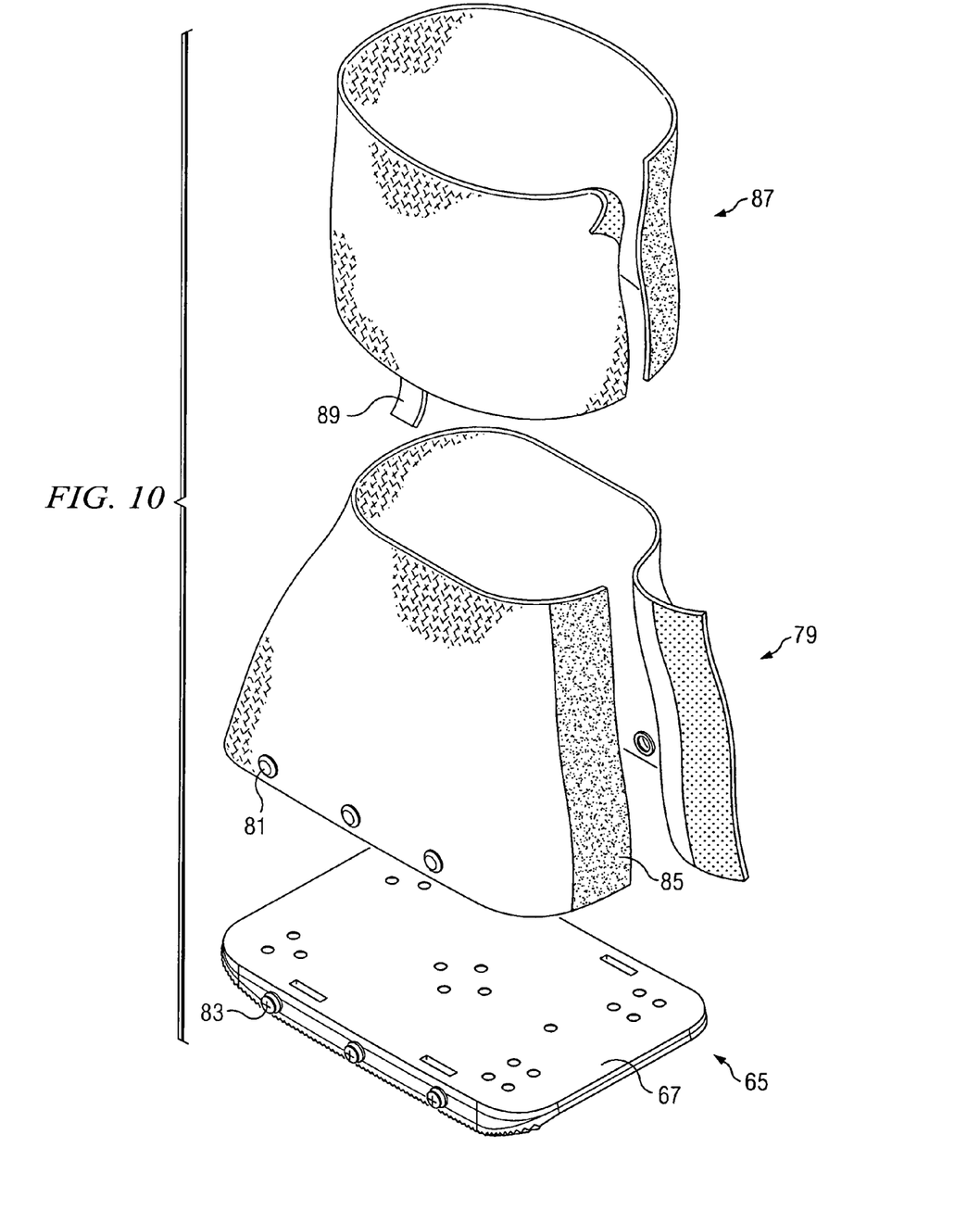
FIG. 10 is a view similar to FIG. 3, but showing an alternate version of the shroud component of the accessory device, the shroud being shown in exploded fashion for ease of illustration.

FIG. 10 of the drawings shows the improved walking plate 65 with an alternative shroud design. The shroud 79 is a one-piece flexible rubber upper layer design having snaps 81 which engage with mating buttons 83 provided on the opposing sides of the walking plate. Its conformability does not require any internal plastic covering or fasteners or loops. It is secured in the back along a vertical seam 85 with Velcro™ materials only upon itself. In the particular example shown in FIG. 10, the basic shroud 79 also has an accompanying upper cuff 87. The cuff can be attached to the upper region of the shroud 79, as by Velcro™ tabs 89.

Figure 5:
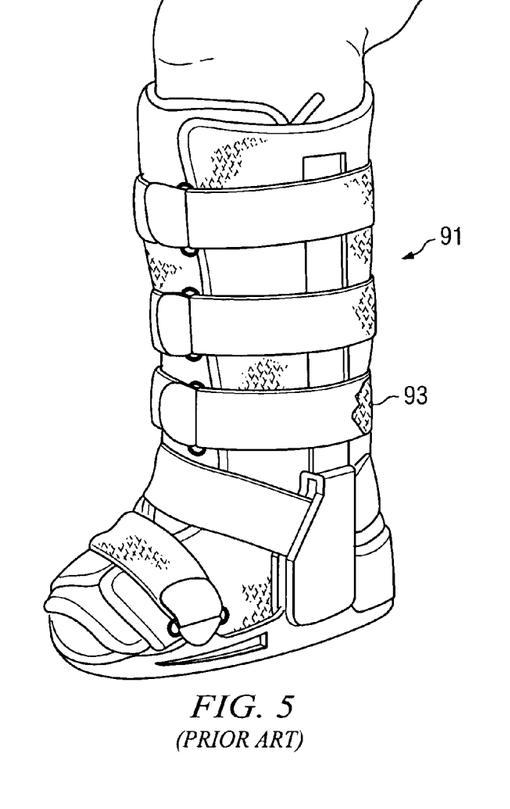
FIG. 5 is view of a prior art cam boot of the type used to stabilize the lower leg of a patient.
Figure 6:
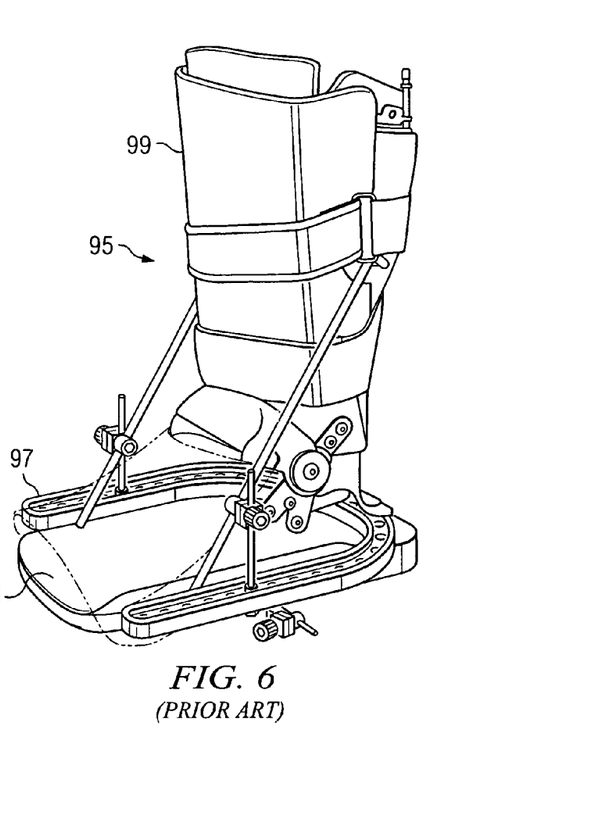
FIG. 6 is a view of another prior art device used to stabilize the lower leg of a patient.
Figure 7:
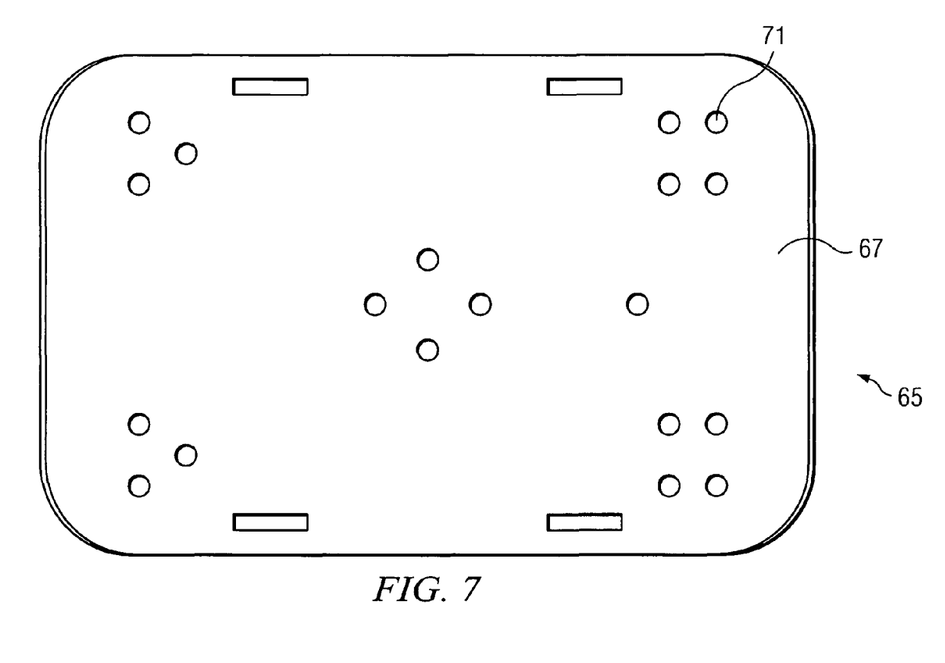
FIG. 7 is a top view of another version of the walking plate component of the accessory device of the invention.

The advantages of the combination accessory device of the invention can perhaps best be understood with reference to the prior art devices shown as FIGS. 5 and 6 of the drawings. FIG. 5 is intended to represent one form of the "cam boot" style of protective boot, designated as 91 in FIG. 5, which is sometimes used as a therapeutic or surgical recovery brace. The cam boot can be seen to resemble a ski boot in outward appearance. In the case of the cam boot shown in FIG. 5, however, the boot functions as a functional splint or cast with a protective sheath and straps 93 which hold the foot in a neutral position while healing takes place. While this type of appliance has the advantages of successfully immobilizing the extremity in certain types of medical situations, and also being removable, the cam boot is not an option when performing surgeries to correct many foot injuries or deformities. Among other differences, the cam boot is completely external and does not feature the internal, transfixation elements that the Ilazarov-type device utilizes.

FIG. 6 illustrates another type of prior art device, generally described in issued U.S. Pat. No. 6,964,663, issued Nov. 15, 2005, to Grant et al., and designated as 95 in FIG. 6. The Grant device has a lower collar element 97 for connection to elements of an Ilizarov-type device. A substantially rigid leg support assembly 99 is adapted to receive a patient's leg, the leg support comprising a cuff and a strap adapted to secure the cuff around the patient's leg. The leg support is rigidly attached to the foot plate 101. The function of the rigid leg support in the device shown in FIG. 6 is obviously to allow the patient's foot to be fixed, with transfixation wires, or pins or screws and simultaneously immobilized with respect to the ankle and lower leg. The rigid leg support is an "internal" feature of the design and does not function to conceal or completely enclose the Ilizarov frame components. In fact, the lower collar component with its associated hardware remains exposed in use. The device would thus fail to provide the esthetic improvement that Applicant's device offers, and fail to provide the type of protection from bumps or other possible injury related occurrences that Applicant's device is intended to provide.

In addition to the above advantages, Applicant's device is simple in design and economical to manufacture. It is comprised of readily commercially available fabrics and materials. The foot plate provides added comfort and protection for the patient's foot, while the shroud completely conceals the Ilizarov fixator components. The shroud is easily removed, as at night, by simply pulling apart the Velcro™ seams. The improved walking plate fits a variety of existing commercially available fixator components. The recessed hole structure, as well as the ambulation angles of the front and rear of the walking plate add to the patients comfort and safety in use.

While the invention has been shown in only two of its forms, it is not thus limited but is susceptible to various modifications without departing from the spirit thereof.

I claim:

1. An accessory device for an external orthopedic fixator used to stabilize a patient's foot and ankle, where the fixator has an external frame made up of a plurality of frame components which surround the lower leg and ankle of a patient with one or more transfixation wires fixed thereto, the accessory device comprising:

a walking plate having an upper surface used for supporting the sole of a patient's foot and having an oppositely arranged lower surface and an intermediate thickness, the walking plate having a plurality of connector elements mounted thereon, the connector elements having exposed upper extents extending upwardly from the upper surface of the foot plate, the upper extents being matingly engageable with at least one of the frame components of the fixator for securing the walking plate to the fixator and for supporting the patient's foot, the walking plate also having a peripheral outer edge which includes a connector region;

a flexible shroud having an overall width and height, an exterior and an interior and a longitudinal seam which allows the shroud to be wrapped about the fixator with the fixator being received within the interior of the shroud, the shroud width and height being sufficient to conceal the fixator when the fixator is so received;

wherein the connector elements which are provided on the walking plate are threaded bolts which have exposed threaded extents which protrude upwardly from the upper surface of the walking plate, and wherein at least one of the frame components of the fixator which is used for securing the walking plate to the fixator and for supporting the patient's foot comprises at least one fixator support collar having a plurality of openings therein, the openings being spaced in alignment with the exposed extents of the threaded bolts for receiving the bolts to thereby attach the walking plate to the fixator support collar;

wherein the walking plate has a plurality of precisely located holes communicating the upper and lower surfaces thereof for receiving the connector elements, the holes being precisely drilled at dimensions measured from four or more different fixator support collars to fit at least three different walking plates, the location of the holes being predetermined to accept a variety of different manufacturer's fixator components of various sizes and spacings without having to inventory a number of different walking plates, or drill additional holes or make other on-site modifications to the walking plate; and wherein the holes which communicate the upper and lower surfaces of the walking plate terminate in counterbores on the plate lower surface, the counterbores being sized to receive the heads of connecting bolts in recessed fashion.

2. The accessory device of claim 1, wherein the bottom surface of the walking plate has a rubber layer which forms a tread pattern for improved traction, the tread pattern being a series of undulating rows running longitudinally between opposing sides of the walking plate.

3. The accessory device of claim 2, wherein the shroud has a lower peripheral edge which is provided with a connector region for matingly engaging the connector region of the walking plate, the longitudinal seam of the shroud also including a connector region for securing the shroud about the fixator, and wherein the connector regions on the lower peripheral edge of the shroud are snaps for engaging mating buttons on opposing sides of the walking plate.

4. The accessory device of claim 3, wherein the connector region provided along the longitudinal seam of the shroud is a mating region of hook and loop type fabric connector fabric, the hook region being present along one exposed edge of the longitudinal seam and the loop region being provided along an oppositely arranged exposed edge of the seam.

5. The accessory device of claim 4, wherein the assembled walking plate and shroud completely enclose the fixator from beneath and on all sides.

6. In combination, a fixator and an accessory device, the combination comprising:

an external orthopedic fixator used to stabilize a patient's foot and ankle, the fixator having an external frame made up of a plurality of frame components which surround a lower leg and ankle of a patient with one or more transfixation wires fixed thereto;

an accessory device made up of a walking plate and a shroud, the walking plate having an upper surface used for supporting the sole of a patient's foot and having an oppositely arranged lower surface and an intermediate thickness, the walking plate having a plurality of connector elements mounted thereon, the connector elements having exposed upper threaded extents extending upwardly from the upper surface of the walking plate, the upper extents being matingly engageable with at least one of the frame components of the fixator for securing the walking plate to the fixator and for supporting the patient's foot, the walking plate also having a peripheral outer edge which includes a connector region;

wherein the connector elements which are provided on the walking plate are threaded bolts which have exposed extents which protrude upwardly from the upper surface of the walking plate, and wherein the frame components of the fixator which are used for securing the walking plate to the fixator and for supporting the patient's walking include at least one support collar having a plurality of openings therein, the openings being spaced in alignment with the exposed extents of the threaded bolts for attaching the walking plate to the fixator collar;

the shroud having an overall width and height, an exterior and an interior and a longitudinal seam which allows the shroud to be wrapped about the fixator with the fixator being received within the interior of the shroud, the shroud width and height being sufficient to conceal the fixator when the fixator is so received, the shroud having a lower peripheral edge which is provided with a connector region for matingly engaging the connector region of the walking plate, the longitudinal seam of the shroud also including a connector region for securing the shroud about the fixator;

wherein the walking plate has a plurality of precisely located holes communicating the upper and lower surfaces thereof for receiving the connector elements, the holes being precisely drilled at dimensions measured from four or more different fixator support collars to fit at least three different walking plates, the location of the holes being predetermined to accept a variety of different manufacturer's fixator components of various sizes and spacings without having to inventory a number of different walking plates, or drill additional holes or make other on-site modifications to the walking plate;

wherein the holes which communicate the upper and lower surfaces of the walking plate terminate in counterbores on the plate lower surface, the counterbores being sized to receive the heads of connecting bolts in recessed fashion wherein the walking plate has a front and rear ambulation cut, each being of a specific angle designed to improve the ambulation of a patient during walking, the walking plate being designed to have an approximate 30 degree angle extending proximally for approximately 2 centimeters back from a toe region of the walking plate and an approximate 15 degree angle extending distally back for approximately 4 centimeters from a heel region of the walking plate, the dimensions being chosen to provide the most natural shape and configuration for ambulation with a foot and ankle locked into a 90 degree position by the associated fixator.

\* \* \* \* \*